US006613224B1

(12) United States Patent
Strand (10) Patent No.: US 6,613,224 B1
(45) Date of Patent: Sep. 2, 2003

(54) LIQUID SEPARATION COLUMN SMART CARTRIDGE

(75) Inventor: David M. Strand, Sherborn, MA (US)

(73) Assignee: Waters Investments Limited, DE (US)

( * ) Notice: Subject to any disclaimer, the term of this patent is extended or adjusted under 35 U.S.C. 154(b) by 0 days.

(21) Appl. No.: 09/680,746

(22) Filed: Oct. 6, 2000

(51) Int. Cl.⁷ .............................................. B01D 15/08
(52) U.S. Cl. .................................... 210/198.2; 210/656
(58) Field of Search ................................ 210/656, 659, 210/198.2, 635

(56) References Cited

U.S. PATENT DOCUMENTS

| | | | | |
|---|---|---|---|---|
| 5,039,409 A | * | 8/1991 | Blaffert | 210/198.2 |
| 5,091,092 A | * | 2/1992 | Newhouse | 210/198.2 |
| 5,738,783 A | * | 4/1998 | Shirota | 210/198.2 |
| 5,872,010 A | | 2/1999 | Karger et al. | 436/173 |
| 5,889,197 A | * | 3/1999 | Van Der Maas | 95/105 |
| 6,035,697 A | * | 3/2000 | Van Der Maas | 210/198.2 |
| 6,332,110 B1 | * | 12/2001 | Wolfe | 210/660 |

OTHER PUBLICATIONS

Edited by: Raymond E. March and John F. J. Todd, Titled: Practical Aspects Of Ion Trap Mass Spectrometry, vol. I—Fundamentals of Ion Trap Mass Spectrometry, 1995, Copyright Information Page & the Page Indicating the Editor–In–Chief.

Authors: Arthur Kantrowitz and Jerry Grey, Titled: A High Intensity Source for the Molecular Beam. Part I. Theoretical, The Review Of Scientific Instruments—vol. 22, No. 5 pp. 328–332, May 1951.

\* cited by examiner

*Primary Examiner*—Ernest G. Therkorn
(74) *Attorney, Agent, or Firm*—Brian Michaelis; John Serio; Brown Rudnick Freed and Cosmer (57) ABSTRACT

A LC column cartridge comprising a memory component integrally attached to it at the time of its manufacture, as well as a method for producing such a LC column cartridge with an integral memory component is disclosed. The memory component is a semiconductor memory chip. The amount of data stored will depend upon the memory capacity of the component, and how the data is recovered will depend on whether or not a microcontroller is incorporated in the component itself. Components could be read only or read/write or be partitioned with a read only area for manufacturing information and a read/write area for usage data. The information stored could vary from the minimal amount of data required to identify the column and its quality control test performance in text format to a full quality control trace and usage history.

9 Claims, 8 Drawing Sheets

LIQUID SEPARATION COLUMN SMART CARTRIDGE

FIELD OF INVENTION

This invention pertains to a liquid chromatography column cartridge, in particular, to a LC column cartridge comprising a memory component.

BACKGROUND

Molecules can be effectively separated by employing liquid chromatography ("LC"). A typical liquid chromatography system consists of a column and solvent which traverses the entire column. As the development of column packing material (also referred to as "stationary phase") progressed, high pressure was required to pump solvent through the column leading to the development of high pressure liquid chromatography (HPLC).

High performance liquid chromatography systems typically consist of high pressure pumps, at least one solvent reservoir, a column capable of withstanding relatively high pressures, and a detector. Columns used in HPLC typically consist of packing material. In most instances this packing material comprises silica-based particles typically with functional groups (defining a column's chemistry) attached to these silica-based particles. The packing of the column is a critical event in the construction of a specific column, for the integrity of the packed bed impacts the overall resolution capability of the column. As the bed becomes disrupted through any series of events, for example, sharp periodic fluctuations in column pressure, resolution will decrease. Maintaining the integrity of the packing bed is essential if the original efficiency capability of a particular column is to be preserved. Through continued usage, the column's packed bed and the bonded phase deteriorate. The resolving power of the column is then lost. Detection and recordation of this loss of resolving power is very important.

Capillary liquid chromatography is a micro-version of traditional liquid chromatography. As is true for traditional liquid chromatography, the column used in capillary liquid chromatography is of critical import. These columns typically have low solvent consumption and require low volumes of sample for analysis. These conditions translate into a higher degree of unit mass detectability. Capillary liquid chromatography systems typically comprise a micro-pumping unit, a capillary column, a detector, and a data processing system. Capillary liquid chromatography columns are typically produced using such materials as fused silica, stainless steel, or polymeric compositions. The lumen of the capillary is packed with packing material containing separation material, such as bonded silica particles. Typically, the internal diameter of the capillary column is between 50 and 500 $\mu$m.

Assessment of column quality is typically performed by running standard analytes through the column and comparing certain chromatographic parameters to a standard test run. Apart from performing a chromatographic run with known analytes, assessment of the column cannot be effectuated. Currently, columns themselves lack the ability to store their performance information which can be of great value. The performance record of a column is very important in environments where quality control is an issue, for example, in the pharmaceutical industry.

SUMMARY

The present invention pertains to a LC column cartridge comprising a memory component integrally attached to it, for example, at the time of its manufacture, as well as a method for producing such a LC column cartridge with an integral memory. In one embodiment, the memory component is a semiconductor memory chip.

The amount of data stored will depend upon the memory capacity, and how the data is recovered will depend on whether or not a microcontroller is incorporated in the component itself. Components could be read only or read/write or be partitioned with a read only area for manufacturing information and a read/write area for usage data. The information stored could vary from the minimal amount of data required to identify the column and its quality control test performance in text format to a full quality control trace and usage history.

The instant invention encompasses at least two types of memory components. One memory component is specific for use on a specific HPLC system. This type of memory component is customized for use with a specific manufacturer's HPLC system. In one illustrative embodiment, the memory component is read and writeable. The read only area comprises full column manufacturing and quality control test data. The writeable area can comprise a history of column usage, for example, number of injections, maximum used pressure, maximum used flowrate, pressure/flow profile, maximum temperature, serial number, as well as other features.

The other memory component can be employed in any HPLC system. In one illustrative embodiment, the memory component is a read only memory component and is supplied with a device to read the memory component and output the data in via, for example, a RS232 interface. The data in this illustrative embodiment can be limited to column manufacturing and quality control test data.

In another illustrative embodiment of the present invention, a method for constructing a liquid separation column smart cartridge is disclosed. An assembled cartridge is provided comprising all of the necessary elements for a smart separation HPLC column including a memory component. The memory component is then programmed at the manufacturing facility. The column is then packed with appropriate packing material based upon the specific use of the column. Following the packing of the column, the column undergoes testing for quality assurance at the manufacturing facility the results of which are then incorporated into the memory component. Following use by an end-user, the column can intermittently throughout its lifetime be examined for quality control issues, for example, in the process of validation of a particular chromatographic method. The column can be tested at a test site, for example, within an end-user's facility, the results of which are then incorporated into the memory component.

This invention provides useful information as to the column's performance which is critical in both Good Manufacturing Practice and Good Laboratory Practice settings. Damaged columns can be detected early, thereby saving on both frustration and useless data acquisition. The present invention provides a user-friendly environment which facilitates compliance with established criteria used in a validated protocol. Full traceability of the column throughout its lifetime is available to the end-user or any other interested party with appropriate access capabilities. This invention provides direct access to information concerning a particular column that has heretofore been unattainable to any end-user.

In accordance with one aspect of the liquid separation column smart cartridge technology disclosed here, an inlet orifice in the housing unit is in fluid communication with a first end of the liquid separation column within the housing and an outlet orifice in the housing unit is in fluid communication with a second end of the liquid separation column. As disclosed above, the liquid separation column provides a fluid flow path within the housing from the inlet orifice to the outlet orifice. First and second ferrule sub-assemblies are fitted to the first and second ends of the liquid separation column, respectively. More specifically, each of the ferrule sub-assemblies comprises a ferrule or end cap seated over the end of the column. The ferrule sub-assembly preferably comprises a compression ring securing the attachment to the liquid separation column. The ferrule sub-assemblies, further described below, each preferably provides a seating and sealing surface for its respective fluid flow port. Preferably the ferrule sub-assembly comprises a frit body providing the seating and sealing surface.

Preferably each of the ferrule sub-assemblies is secured to the housing in a fixed position, optionally being removably fixed, at its respective port. In this manner, the liquid separation column can be conveniently anchored to the housing, e.g., to a component of the housing which is assembled with one or more other housing components after the liquid separation column is attached, to construct the housing unit of the smart cartridge. More specifically, in accordance with certain illustrative embodiments, a surface of the ferrule sub-assembly at the inlet end of the liquid separation column is a substantially flat surface having a fluid opening for the inlet port and facing substantially outwardly from the housing to seat and seal conveniently against a corresponding surface of a fluid feed line or other fluid source feeding fluid to the liquid separation column smart cartridge for testing, analysis, etc. Similarly, a surface of the ferrule sub-assembly attached to the outlet end of the liquid separation column provides a substantially flat surface having a fluid opening for the outlet port and facing substantially outwardly from the housing to seat and seal conveniently against a corresponding surface of a fluid return or waste line or other fluid receiving device for accepting fluid from the liquid separation column smart cartridge after it has been tested, analyzed or subjected to other operation(s) by the liquid separation column within the housing. It should be recognized that the designation of a port of the housing unit as being an inlet port or an outlet port may in certain instances be arbitrary and merely a matter of convenience or choice, such as where the smart cartridge is usable in either direction, preferably then being side-to-side symmetrical so that it can be properly installed in either orientation. In another illustrative embodiment of the present invention, an outwardly extending connector is provided on a liquid column separation smart cartridge to enable insertion of the smart cartridge fluid ports into wells or receiving sockets of a manifold or mounting device or the like, for fluid connection and sealing.

BRIEF DESCRIPTION OF THE FIGURES

The foregoing and other features and advantages of the present invention will be more fully understood from the following detailed description of an illustrative embodiment, taken in conjunction with the accompanying drawings in which.

DETAILED DESCRIPTION

An illustrative embodiment of the present invention pertains to a liquid separation column smart cartridge. It will be recognized by those skilled in the art that liquid separation smart cartridges disclosed and described here can be adapted to function in accordance with various different liquid separation test or analysis methods. Liquid separation method parameters can be stored in the memory component of the smart cartridge and, in accordance with an illustrative embodiment, such information stored in the memory component defines a liquid separation method such as, for example, liquid chromatography (LC), capillary electrophoresis (CE) or other liquid-phase separation techniques, e.g., mycellular electrokinetic chromatography (MEKC or MECC), isoelectric focusing and isotachophoresis (ITP). For convenience, and not intending to limit the scope of the smart cartridge technology disclosed here, much of the following detailed description of illustrative embodiments will take liquid chromatography as the separation method to be performed by the smart cartridge.

An illustrative embodiment of the present invention pertains to a liquid separation column smart cartridge. The cartridge comprises an exterior an interior portion. The exterior portion comprises a housing unit 1 which comprises a base plate 2, at least two side plates 3, a rear manifold 4 which is perpendicular to the two side plates, a front manifold 5 that lies perpendicular to the two side plates, a cover plate 6 and a memory component 23. See FIG. 1.

An input 7 and an output 8 orifice are also incorporated in this illustrative embodiment. In this embodiment, both the input 7 and output 8 orifices are disposed within the front manifold 5. The input 7 and output 8 orifices comprise fittings (9, 10, see FIG. 2) which are used to facilitate entry and exit, respectively, of a solvent, with or without sample, through the cartridge. The fittings 9, 10 can have an exterior surface aspect and an inner surface aspect. The outer (or exterior) surface aspect interfaces with an exterior connection, such as a LC column (20, see FIG. 2) carrying solvent. The inner (or interior) surface aspect interfaces with the interior of the housing unit 1. The fitting is secured within an orifice by any means known to those skilled in the art.

An LC column 20 is housed within the interior of the housing unit 1 with two defined ends is attached at a first end 21 to the input orifice fitting 9 and at a second end 22 attached to the output orifice fitting 10. See FIG. 2. The means for attachment are well known to those skilled in the art. In an illustrative embodiment, the input 9 and output 10 orifice fittings are coated with a substance in order to maintain a tight seal, that is, to exclude any fluid from permeating between the junction formed by an orifice fitting and surface of the manifold. An example of such a sealing substance that can be used in the present invention is polytetrafluorethylene.

Figure 2:
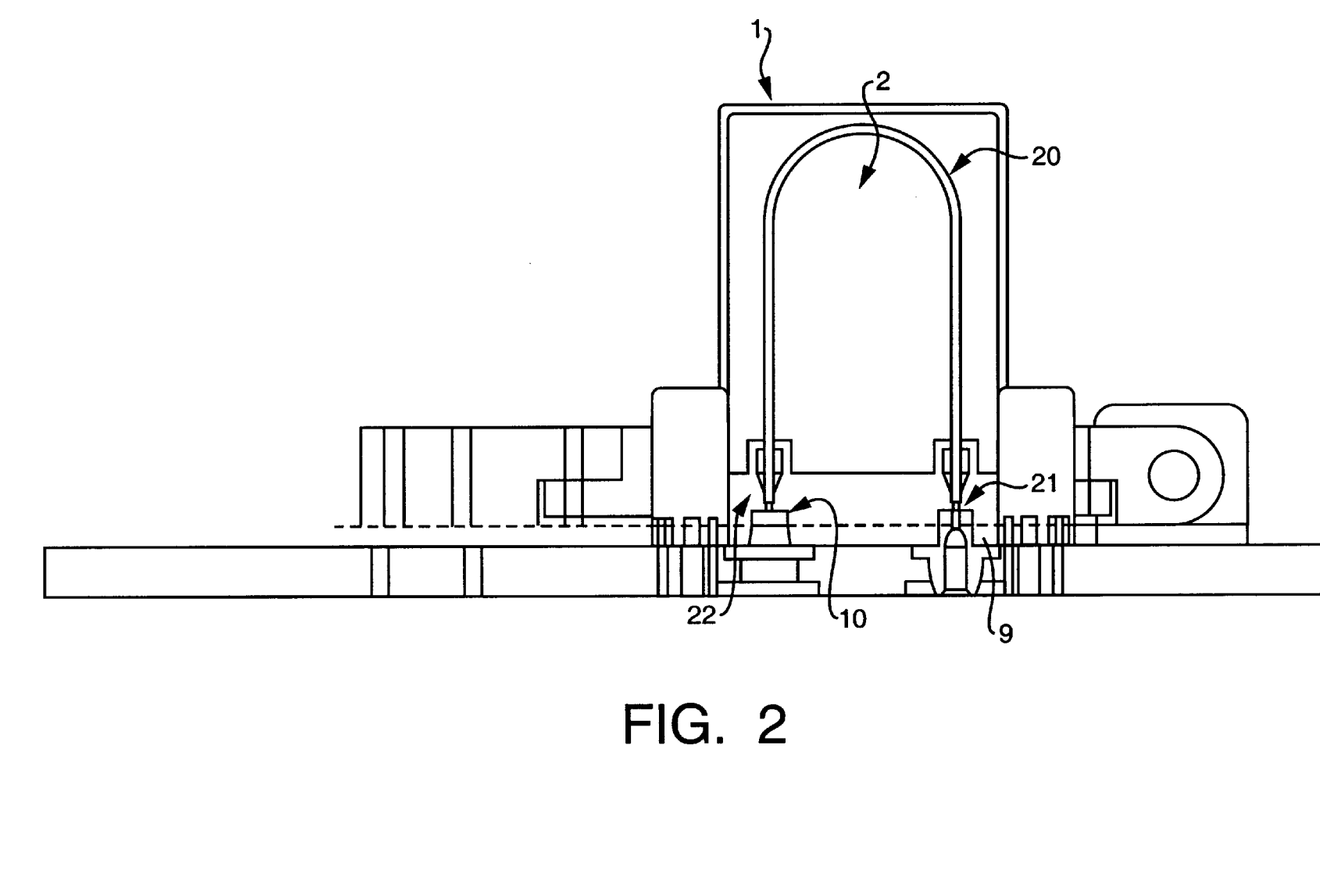
FIG. 2 is a cut-away view of the liquid separation column smart cartridge shown in FIG. 1.

In the illustrative embodiment of the present invention, a capillary column is used. The capillary column is defined by a tube having a lumen with a first and second end. The material which comprises the capillary column can include, but is not limited to, fused silica, glass, polyetheretherketone (or PEEK), as well as other polymeric materials well known in the art. The first end of the capillary tube can interface with the inner surface aspect of the input orifice fitting (that is, the surface aspect which is interior within the housing unit), while the second end can interface with the inner surface aspect of the exit orifice fitting. The length of the capillary column in the present embodiment can range from about 6 cm to about 25 cm.

Figure 1:
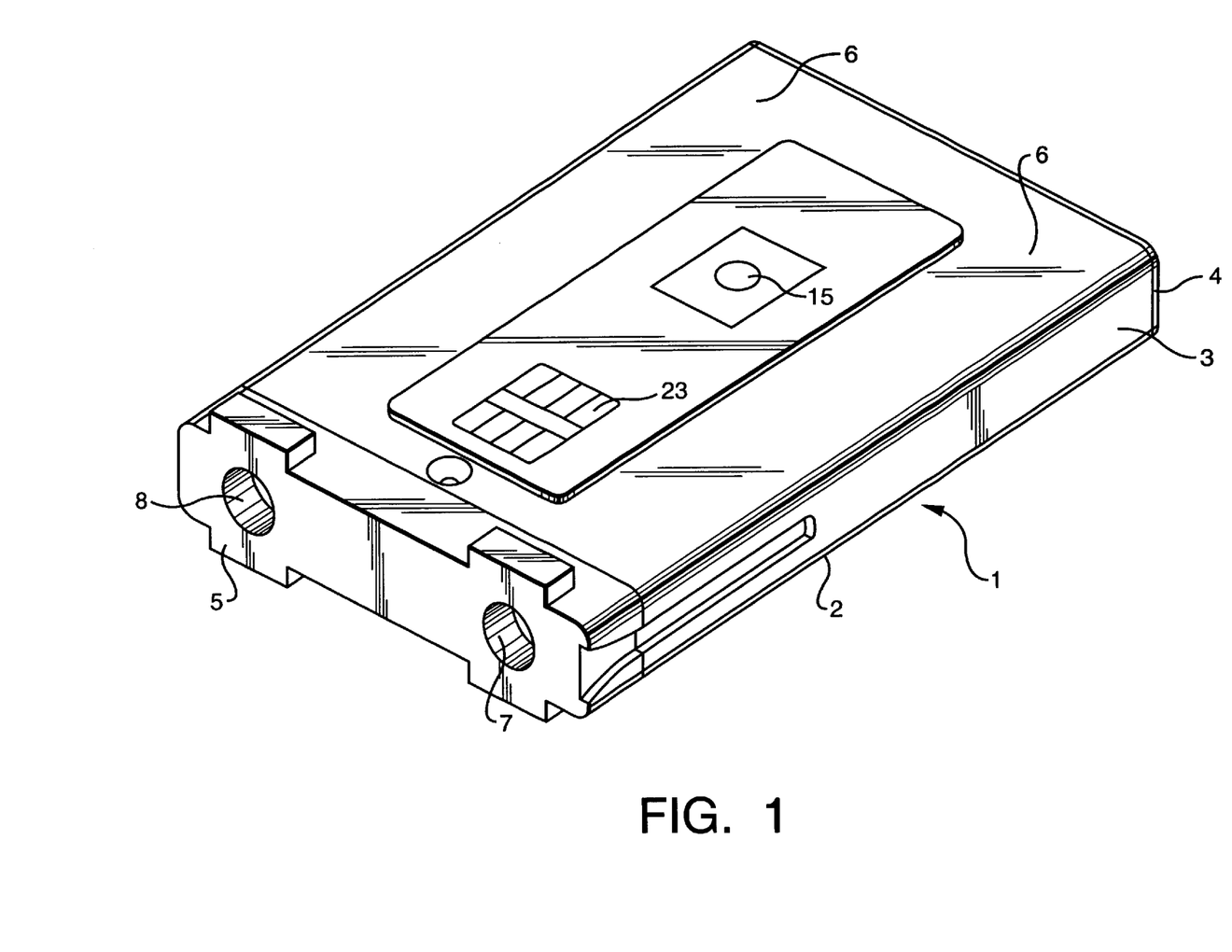
FIG. 1 is a perspective view of a liquid separation column smart cartridge according to the invention.

The rear 4 and front 5 manifolds can be positioned and secured into place with the remaining housing unit 1 by means well known to those skilled in the art. The means for securing the manifolds 4, 5 to the housing unit 1 can include, but are not limited to, employing an adhesive agent, a screw forming a male unit which is then placed in apposition with a female union, a preformed male connector placed in apposition with a female union, and alike.

The external portion of the cartridge comprises at least one electrical connector (not shown). In an illustrative embodiment, the front manifold comprises a female electrical connector. In another illustrative embodiment, a display unit 15, such as a liquid crystal display, is inserted within or atop an outer surface of the housing unit, such as the cover plate 6. See FIG. 1. This display unit 15 is connected to a memory component housed within the housing unit 1.

Figure 3:
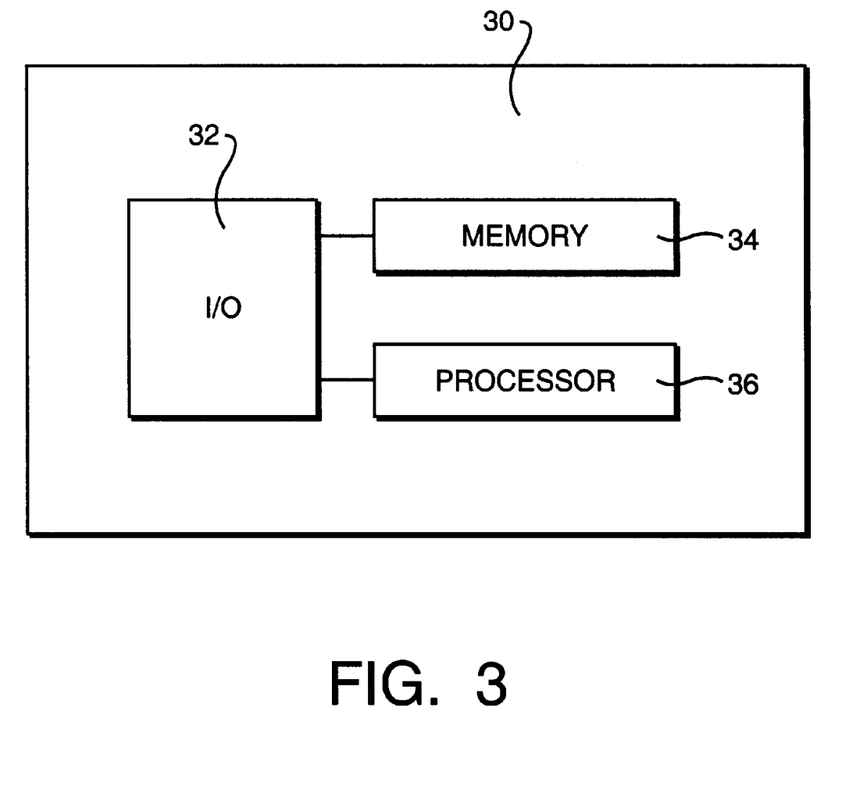
FIG. 3 is a block diagram of a circuit board contained within the housing of a liquid separation column smart cartridge.

In one embodiment of the instant invention, the base plate 2 comprises at least one read-write memory chip 30. See FIG. 3. Examples of different types of suitable memory chips are well-known in the art, such as a Dallas Semiconductor chip DS1994 4K-Bit Plus Time Touch Memory. Suitable memory chips typically include an Input/Output portion 32 along with memory 34 and optionally may include a processor 36.

Figure 4:
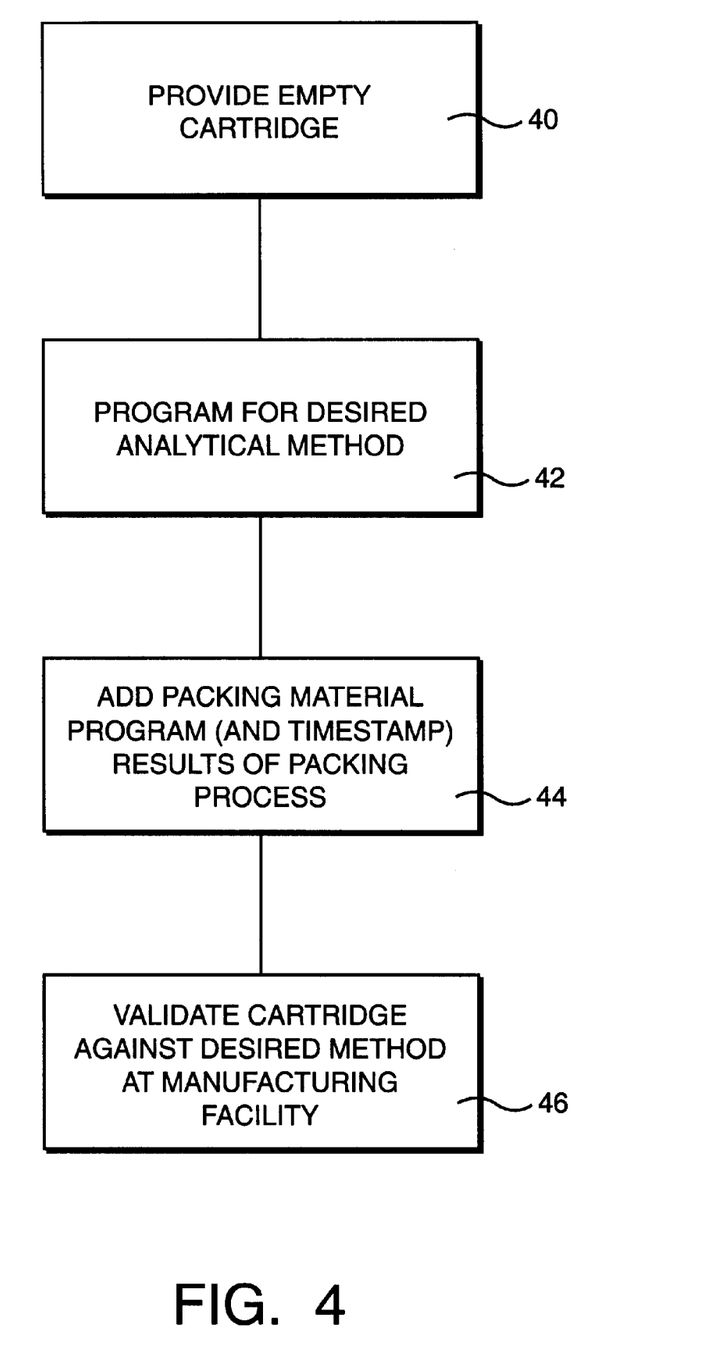
FIG. 4 is a flow diagram of the method of producing a liquid separation column smart cartridge, according to the invention.

A method for the construction of a liquid separation smart cartridge according to the invention is illustrated in FIG. 4. In this embodiment, an assembled cartridge 40 capable of performing chromatography is provided, which comprises a memory component 42 as described herein before. Liquid separation method parameters are stored in the memory component 42 for example, while at the manufacturing site. The type of information written into the memory component when it is "personalized" for a particular user method can include, but is not limited to, method parameters defining a chromatographic (LC) or capillary electrophoretic (CE) or other liquid-phase separation, such as mycellular electrokinectic chromatography (MEKC or MECC) separation to be employed by the particular smart separation cartridge, including data acquisition parameters, solvent gradient control parameters, expected target molecule names, IUPAC identifiers and retention time windows, detector response factors, other operational and analytical parameters used by commercial chromatographic data stations, other information desirable to an end-user and the date and time of method personalization.

Subsequently, test performance (also known as method validation) data would typically be stored to the memory component with the time and date obtained. The memory component is capable of storing acquired data in its memory with an indicator of column usage. Examples of different types of read/writeable memory chips (used interchangeably with "memory component") are well known in the art. It should be appreciated that information stored onto the memory component can be encrypted.

The coded information can be in the form of a bar code, a magnetic strip, or semiconductor chip. The device employed to read the code from the liquid separation column smart cartridge will depend on the format and medium of the code contained within the memory component, examples of which include, but are not limited to, bar code reader, a magnetic strip reader, a radio transponder, an inductive loop, ultra-sonic, infra-red, direct connection, an optical detector, electrical impulse detector or a data bus socket, all of the aforementioned means are well known to those skilled in the art. To access the code, there can be security procedures which must be complied with or access is denied.

An example of this type of data storage capability is one which has a built-in program. Within each card there is a region of non-volatile memory, or EEPROM. This memory is divided into a number of directories. Each directory has an identification number associated with it. The directories can contain a number of files and a file descriptor components. Stored information can be communicated with the outside world in either "clear" or "encrypted" mode. The choice is at the discretion of the reader depending on how important the data is and how vulnerable it is to attack. All files have a set of attributes associated with them. This attribute information describes the permissions required to access the associated file. In this example, memory is allocated in blocks to the directories. The number and size of these directories is at the control of the distributor within the limits of the memory component's memory. Each directory contains a file descriptor component, a record of unallocated file space and a password.

The liquid separation column smart cartridge comprises packing material 44 conveying a specific chemistry identity to the column. Typically, the column is packed at the manufacturing facility. The specific chemistry to be used for a given column can be determined by the programmed method already installed into the memory component. For example, if the memory component contains a chromatographic separations method for anion exchange, then the packing material could comprise silica-based particles comprising cationic chemistry. Procedures for packing columns whether they are capillary columns or standard HPLC analytic columns is well known in the art.

The assembled and packed liquid separation column smart cartridge can be tested at the manufacturing site 46 to determine whether the column complies with known specifications pertinent to a particular chromatographic method. For example, known analytes specific for a particular chemistry can be subjected to chromatographic separation using the newly formed liquid separation column smart cartridge. Resolution, along with other chromatographic parameters, can be determined based upon the performance of the column with a given set of known analytes. This is a similar operation to that performed when validating a chromatographic method where measuring the performance of a column is of critical import. The information obtained from this testing can then be stored in the memory component. This test information can subsequently be used as a benchmark for determining the performance status of the column once the apparatus has left the manufacturing facility and is in the hands of an end-user, for example, in system suitability. If the column meets approval, then the apparatus as a whole can be certified in digital format stored in the memory component by the manufacturer.

The column according to the present invention encompasses at least two types of memory components. One memory component is specific for use on a specific HPLC system. This type of memory component is customized for use with a specific manufacturer's HPLC system. In one illustrative embodiment, the memory component is read and writeable. The read only area comprises full column manufacturing and quality control test data. The writeable area can comprise a history of column usage, for example, number of injections, maximum used pressure, maximum used flowrate, pressure/flow profile, maximum temperature, as well as other features. When the column comprising a memory component is placed in a particular instrument, the column details are read into the instrument and the HPLC instrument sets-up according to the method contained within the memory component. This allows for non-expert operators to perform an analysis without having to program the HPLC system. On completion of the analysis, the column's usage information, for example, flow rate, pressure, analysis method, number of injections, last calibration run date and reference, last used date and the like, can be updated and encoded into the memory component.

The other memory component can be employed in any HPLC system. In one illustrative embodiment, the memory component is a read only memory component and is supplied with a device to read the memory component and output the data in via, for example, a RS232 interface. The data in this illustrative embodiment can be limited to column manufacturing and quality control test data.

In general, the types of information that can be stored into the memory component includes all parameters that describe the column materials, geometry and construction; also, all parameters that describe any packings, coatings or accessory chemistries, such as, filters and guard columns. Time stamp information can also be encoded into the memory component. This information can be stored at the time the column is manufactured. Additional information that can be stored pertains to the method to be employed by the liquid separation column smart cartridge. Each liquid separation column smart cartridge is designed for a given application and dedicated to that use for the life of a particular column. Information that can be stored on the memory chip includes standard overall separation parameters, such as run time, data acquisition, and sampling rate. Also, the names and expected retention times and retention time windows for the target and/or expected analytes which will be eluted from the column during the separation run can be stored in the memory component. Parameters and expected results sufficient to validate the column and/or method against a standard separation run for the programmed method using a prepared standard solution can also be part of the information portfolio of the memory component. As mentioned previously, the operating history can be stored in the memory component. Such information includes, but is not limited to, the number of injections, performance statistics for each injection, such as, the measured peak width for a reference peak, information concerning any significant deviations, information regarding improper usage, such as, the use of the column with inappropriate solvents, as well as other information.

Throughout the lifetime of the liquid separation column smart cartridge, various information can be stored on the memory component. For example, the number of injections, maximum used pressure, maximum used flowrate, pressure/flow profile, maximum temperature, can be stored within the memory component. This information can be later accessed by a test center or at the manufacturing facility. Performance status can also be measured by subsequent testing of the column's ability to facilitate separation of test analytes. This can be compared to the test analysis performed at the manufacturing facility prior to delivery of the liquid separation column smart cartridge to an end-user. This capability allows for lifetime validation of the column. Potentially the column may be passed along to several end-users, however, the data stored within the memory component, which is an integral component of the column apparatus, will stay with the column. Therefore, there is no concern that as a column gets passed along between end-users, that the data critical for validation will get lost amidst the column's sojourn.

As disclosed above, in accordance with certain illustrative embodiments of the liquid separation smart cartridge disclosed here, ferrule assemblies are employed as fittings on the ends of the liquid separation column. The ferrule assemblies are received into correspondingly sized sockets in the housing unit, preferably with a friction fit or, alternatively, with a snap-fit, with adhesive or other means to form a permanent or removably fixed connection between the ferrule and the housing. The ferrule fittings in this way serve to anchor the ends of the liquid separation column to the housing of the smart cartridge. Preferably, the ferrule fittings are received into an end plate of the housing unit, with the two ends of the liquid separation column extending back through the end plate into the interior of the housing formed by an open-ended concave housing member attached to, and closed by, the end plate. The ferrule assemblies advantageously provide an externally facing seating and sealing surface for fluid flow into or out of the liquid separation column.

The ferrule is in the form of a cap, preferably being formed of metal or other suitable material. An annular wall extending from an end wall of the ferrule forms a socket into which the end of the liquid separation column is inserted. Preferably the ferrule socket forms a tight fit with the column. A compression ring seats around the exterior of the annular wall. The compression ring, as its name suggests, is sized to compress the ferrule socket on the end of the column to secure it in place. Preferably the end of the annular wall is beveled or chamfered to ease its insertion into the compression ring. The compression ring typically has a somewhat conical inside wall, larger toward the end wall of ferrule, such that its fit around the annular wall of the ferrule gets tighter as it is forced on.

The ferrule has a fluid flow passage extending through the end wall, whereby fluid can flow to or from the liquid separation column through the end wall. The ferrule subassembly in accordance with illustrative embodiments further comprises a frit body at the exterior surface of the end wall to provide a seating and sealing surface. In accordance with illustrative embodiments, the frit body is seated in a well in the exterior face of the ferrule over the end of the fluid flow passage, optionally standing slightly proud of the exterior face of the ferrule, to serve as a seating and sealing surface. In use, a fluid delivery line or fluid removal line mated to the smart cartridge to establish delivery and removal of fluid to be tested by the smart cartridge, can be pressed against the frit body to establish a fluid tight seal with a sufficient degree of give or resiliency to accommodate manufacturing tolerances, dissimilar temperature expansion coefficients and the like.

Figure 5:
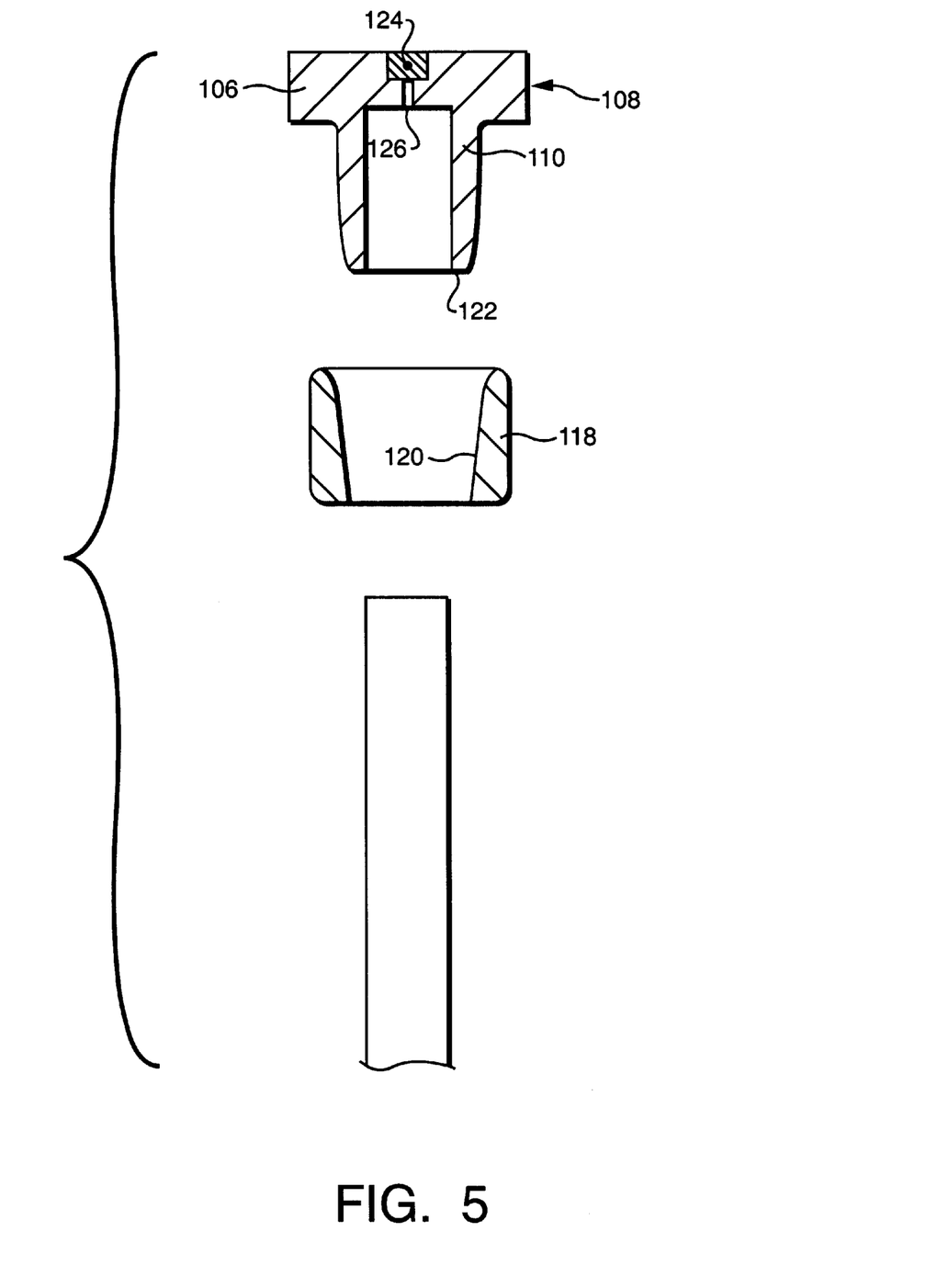
FIG. 5 is an exploded section view of a ferrule sub-assembly in accordance with the present invention.
Figure 6A:
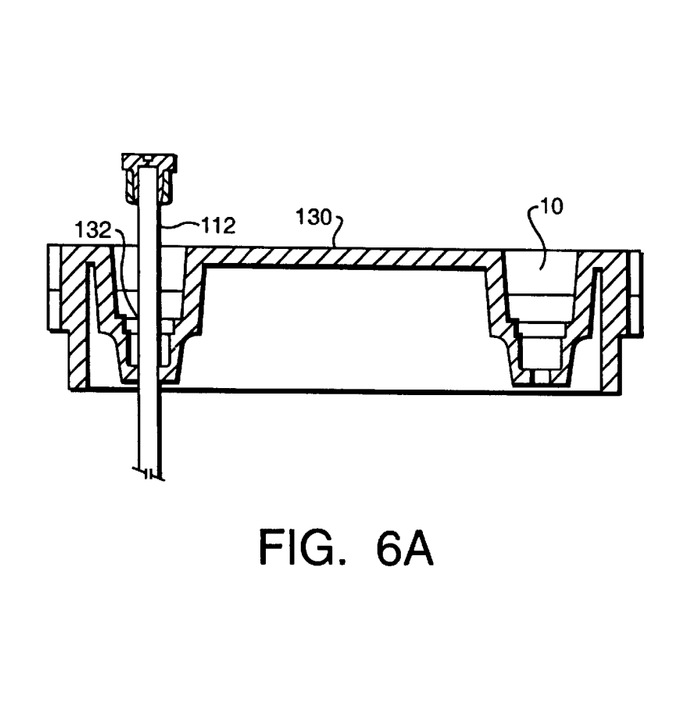
FIGS. 6a and 6b are schematic section views, partially broken away, showing the ferrule sub-assembly of FIG. 4 in use in a smart cartridge in accordance with the present disclosure.
Figure 6B:
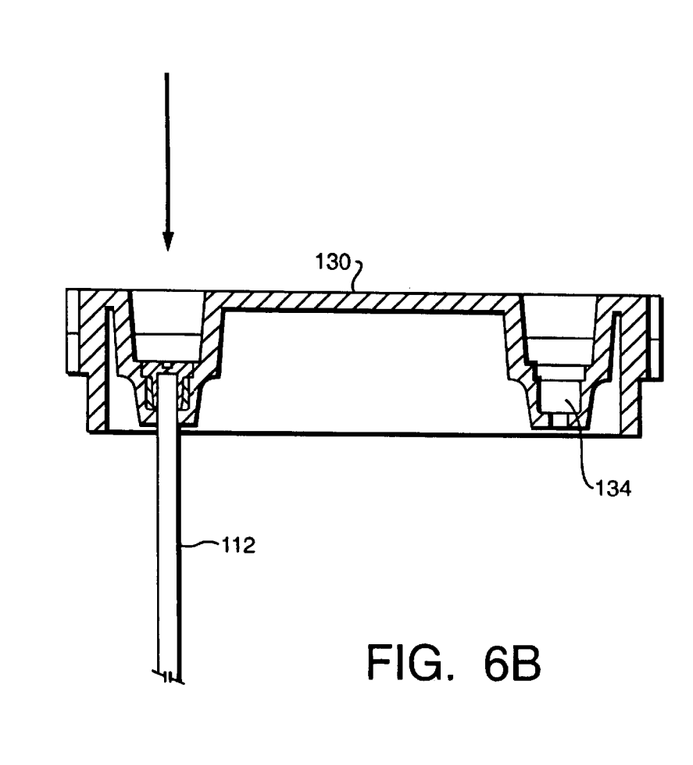

Referring now to FIG. 5, a ferrule sub-assembly 102 shown in exploded view to comprise a ferrule 104 having an end wall 106 with an exterior surface 108 and an annular wall 110 forming ferrule socket 111 to receive the end of liquid separation column 112. While the drawings are not necessarily to scale, inside surface 114 of annular wall 110 is sized to form a friction fit or other tight fit with exterior surface 116 of liquid separation column 112. Compression ring 118, preferably being formed of stainless steel or other suitable material, has a slightly conical inside surface 120. The beveled end 122 of annular wall 110 eases insertion of the annular wall into the compression ring. Fitting the compression ring onto annular wall 110 tightens the fit around the liquid separation column. Frit body 124 is seen to be seated in well 126 in the exterior surface 108 of end wall 106 of ferrule 104. The frit body stands slightly proud of the exterior surface 108, that is, it extends beyond exterior wall 108 slightly. Referring now to FIGS. 6a and 6b, a ferrule sub-assembly 102 as described above it is seated on liquid separation column 112 which extends through end plate 130 of a smart cartridge. It can be seen that socket 132 in end wall 130 will receive ferrule sub-assembly 102. Typically, the assembled structure shown in FIG. 6a is pressed into socket 132 using any suitable mechanical device and/or pulled in by the liquid separation column. The result is seen in FIG. 6b, wherein the ferrule sub-assembly is seated in socket 132 and liquid separation column 112 extends rearwardly into the housing unit of the smart cartridge. While, for simplicity of illustration, the second end of liquid separation column 112 is not shown, it will be readily understood by those skilled in the art that a ferrule sub-assembly similar to or the same as sub-assembly 102 described above can be fitted to the second end of the column and seated in socket 134 of the housing end wall 130.

Figure 7A:
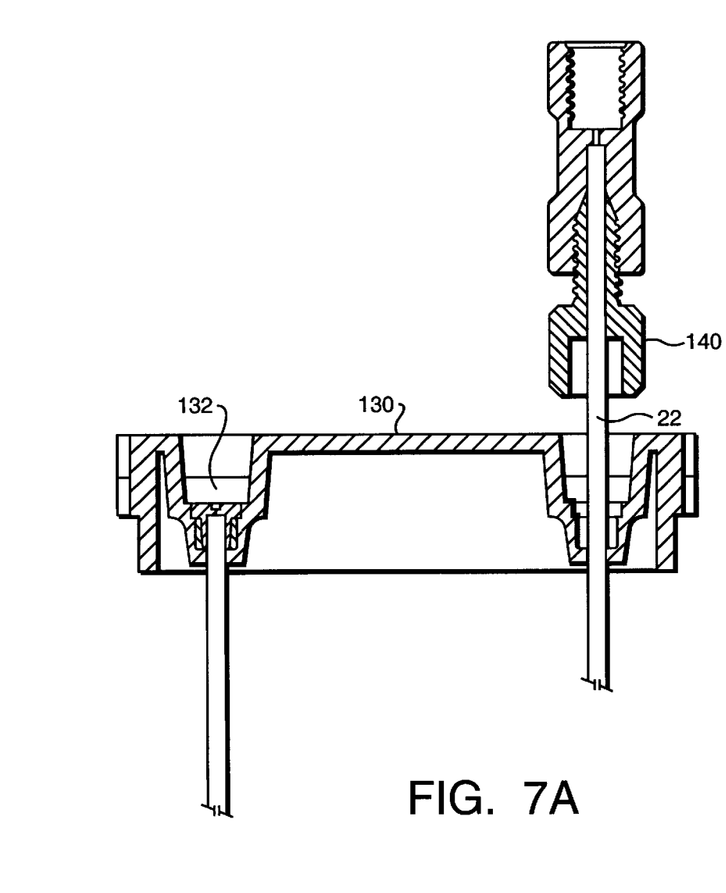
FIGS. 7a and 7b are schematic section views, partially broken away, showing the liquid separation column of a smart cartridge in accordance with the present disclosure, comprising ferrule sub-assemblies in accordance with the embodiment of FIG. 4, being charged with liquid separation media.
Figure 7B:
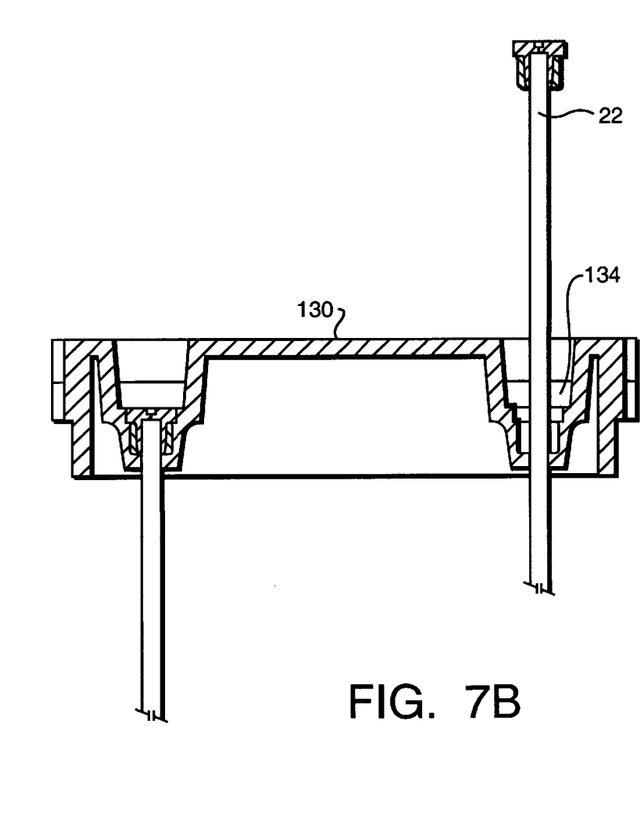

In accordance with certain illustrative embodiments, FIG. 7a shows packing of the column material. A device 140, preferably a needle with a syringe or tubing, is connected to the open end of a liquid separation column 22. It can be seen that the first end of the liquid separation column, fitted with a ferrule sub-assembly as described above, is already seated in socket 132 of the manifold or end plate 130 of the housing unit of the smart cartridge. After loading the column material, an additional ferrule sub-assembly is added to the second end of the column 22 (see FIG. 7b). The second end of the column is then pressed into socket 134 of the housing unit using mechanical or other means, as discussed above (see FIG. 6b).

Figure 8:
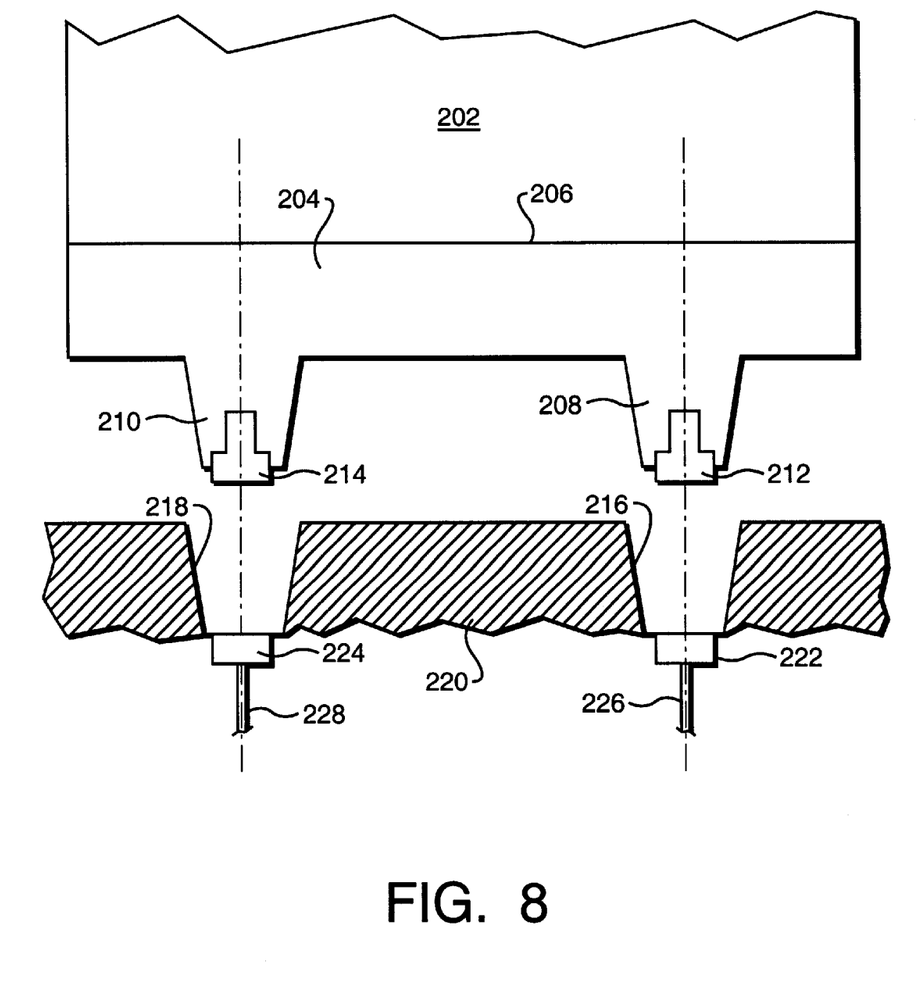
FIG. 8 is an exploded schematic view, partially broken away, showing a smart cartridge in accordance with another illustrative embodiment of the present disclosure, comprising ferrule sub-assemblies in accordance with the embodiment of FIG. 4 mounted in fluid ports extending outwardly from an end cap or manifold of the housing unit of the smart cartridge.

Referring now to FIG. 8, an alternative illustrative embodiment is illustrated of the liquid separation column smart cartridge. A housing unit of the smart cartridge comprises an endplate 204 secured at interface 206 to an open-ended concave housing component 202. A liquid separation column (not shown) is located within the housing component 202. The first end of the column terminates at a ferrule sub-assembly 212, such as described above. The second end of the liquid separation column terminates at ferrule sub-assembly 214. Thus, ferrule sub-assembly 212 forms an inlet orifice and ferrule sub-assembly 214 forms an outlet orifice for the smart cartridge. As seen in FIG. 8, the inlet orifice is located in outwardly extending projection 208 of the endplate 204. The liquid separation column extends rearwardly (or upwardly as seen in FIG. 8) through the endplate 204 into the housing chamber formed by housing component 202. Similarly, the outlet orifice formed by the ferrule sub-assembly 214 is located in outwardly extending projection 210 of the endplate 204, and the second end of the liquid separation column passes through endplate 204 to ferrule sub-assembly 214 at the outward end of projection 210.

In accordance with the illustrative embodiment illustrated in FIG. 8, the first and second outwardly extending projections 208, 210 each is substantially frustro-conical and symmetrical about the axis of the inlet and outlet orifices, respectively. Preferably the housing unit is generally planer, having its smallest dimension into the plane of the paper as viewed in FIG. 8. In accordance with such illustrative embodiments, the outwardly extending projections preferably are substantially symmetrical and parallel projects generally in the plane of the housing unit.

While a particular form of the invention has been fully illustrated and described, it will be obvious to those skilled in the art that various modifications and alteration may be made therein and it is intended to cover all such modifications and alterations as may fall within the spirit and scope of the invention.

What is claimed is:

1. A liquid separation column smart cartridge, comprising:
    a housing unit, wherein said housing unit comprises:
        an inlet orifice disposed within said housing unit;
        an outlet orifice disposed within said housing unit;
        a liquid chromatography column connecting said inlet orifice to said outlet orifice; and
        a memory component disposed within said housing unit, said memory component containing liquid chromatography separation method parameters that direct operation of a chromatographic instrument said parameters that direct operation include at least one of number of injections, maximum used pressure, maximum used flow rate, pressure/flow profile, maximum temperature.

2. The cartridge of claim 1, wherein said memory component is read only.

3. The cartridge of claim 1, wherein said memory component includes a writeable area that contains history of column usage and said readable area contains full column manufacturing and quality control test data.

4. The cartridge of claim 1, wherein said memory component containing said liquid chromatography separation method parameters is specific for a specific HPLC system.

5. The cartridge of claim 1, wherein said memory component further comprises a processor.

6. The cartridge of claim 1, wherein said memory component is a semiconductor memory.

7. The cartridge of claim 1, further comprising a display unit.

8. The cartridge of claim 7, wherein said display unit is a liquid crystal display unit.

9. The cartridge of claim 1, wherein information stored on said memory component is encrypted.

\* \* \* \* \*